United States Patent
Du et al.

(10) Patent No.: US 12,053,394 B2
(45) Date of Patent: Aug. 6, 2024

(54) DEVICE, KIT FOR REPAIRING AND FIXING ARTICULAR CARTILAGE, AND METHOD FOR THE SAME

(71) Applicant: Shanghai Sixth People's Hospital, Shanghai (CN)

(72) Inventors: Dajiang Du, Shanghai (CN); Changqing Zhang, Shanghai (CN)

(73) Assignee: Shanghai Sixth People's Hospital, Shanghai (CN)

( * ) Notice: Subject to any disclaimer, the term of this patent is extended or adjusted under 35 U.S.C. 154(b) by 506 days.

(21) Appl. No.: 17/462,149

(22) Filed: Aug. 31, 2021

(65) Prior Publication Data
US 2022/0226128 A1 Jul. 21, 2022

(30) Foreign Application Priority Data
Jan. 20, 2021 (CN) .......................... 202110077845.0

(51) Int. Cl.
| | |
|---|---|
| A61F 2/46 | (2006.01) |
| A61B 17/16 | (2006.01) |
| A61F 2/30 | (2006.01) |
| A61L 27/26 | (2006.01) |
| A61L 27/36 | (2006.01) |

(52) U.S. Cl.
CPC ........ *A61F 2/4618* (2013.01); *A61B 17/1693* (2013.01); *A61F 2/30756* (2013.01); *A61L 27/26* (2013.01); *A61L 27/3612* (2013.01)

(58) Field of Classification Search
CPC .............. A61F 2/4618; A61F 2/30756; A61B 17/1693; A61L 27/26; A61L 27/3612
USPC .......................................... 606/80–86, 96, 99
See application file for complete search history.

(56) References Cited

U.S. PATENT DOCUMENTS 4,147,164 A * 4/1979 Behney ..................... A61F 2/18
606/1
5,211,644 A * 5/1993 VanBeek ............ A61B 17/3468
606/1
(Continued)

FOREIGN PATENT DOCUMENTS

| CN | 104174068 A | 12/2014 |
|---|---|---|
| CN | 112842451 A | 5/2021 |

(Continued)

*Primary Examiner* — Jessica Weiss
(74) *Attorney, Agent, or Firm* — Harness, Dickey & Pierce, P.L.C.

(57) ABSTRACT

The invention provides a device, a kit for repairing and fixing articular cartilage, and a method for the same. The device comprises a costal cartilage rod, an outer sleeve, a drilling part, and an auxiliary implantation component; the drilling part comprises a drill sleeve and a drill bit matching an inner diameter of the drill sleeve; the auxiliary implantation component comprises a cartilage rod sleeve and an auxiliary pushing element, the costal cartilage rod has a rod-shaped structure with a diameter ranging from 3 mm to 8 mm and less than an inner diameter of the cartilage rod sleeve, and the costal cartilage rod is obtained from processing of costal cartilage. The costal cartilage is selected from the group consisting of autologous costal cartilage, allogeneic costal cartilage, or xenogeneic costal cartilage. Costal cartilage is processed into a costal cartilage rod by using the device provided in the present invention.

10 Claims, 6 Drawing Sheets

(56) References Cited

U.S. PATENT DOCUMENTS

| | | | | |
|---|---|---|---|---|
| 5,921,987 A * | 7/1999 | Stone | A61F 2/30756 | 606/80 |
| 11,751,944 B2 * | 9/2023 | Lang | A61B 90/37 | 606/130 |
| 2001/0039455 A1 * | 11/2001 | Simon | A61F 2/30767 | 623/18.11 |
| 2005/0137600 A1 * | 6/2005 | Jacobs | A61B 17/1631 | 606/79 |
| 2009/0299371 A1 * | 12/2009 | Steiner | A61B 17/1675 | 606/87 |
| 2010/0312102 A1 * | 12/2010 | Barnes | A61B 17/3211 | 600/424 |
| 2014/0114330 A1 * | 4/2014 | Karasic | A61B 17/0401 | 606/144 |
| 2015/0072018 A1 * | 3/2015 | Rosines | A61L 27/3687 | 435/395 |
| 2020/0337847 A1 * | 10/2020 | Zhang | A61L 27/3817 | |

FOREIGN PATENT DOCUMENTS

| | | | |
|---|---|---|---|
| EP | 0 346 033 A1 | 12/1989 | |
| WO | WO-2009011849 A2 * | 1/2009 | A61B 17/1604 |

* cited by examiner

DEVICE, KIT FOR REPAIRING AND FIXING ARTICULAR CARTILAGE, AND METHOD FOR THE SAME

CROSS-REFERENCE TO RELATED APPLICATIONS

This application claims priority to Chinese Patent Application No. 202110077845.0, filed on Jan. 20, 2021. The entire disclosure of the application identified in this paragraph is incorporated herein by reference.

FIELD

The invention relates to the field of medical technology, and more particularly, to a device, a kit for repairing and fixing articular cartilage, and a method for the same.

BACKGROUND

Bone nails are used for internal fixation of fractures in any part of the body and spines, for example, especially for holding bone pieces together. The prior art No. EP89305627.5 discloses a bone nail, wherein the bone nail is designed to be inserted into the part needs to be fixed in a form of a bone rod for solving the problem that the bone pieces are prone to be displaced after the drill is removed. In addition, the bone nail is made from polymer materials that can be absorbed by the body. However, the product provided in this patent has biological histology and mechanical properties that are substantially different from those of articular cartilage, therefore, it cannot effectively repair and fix the bone cartilage of articular surface.

Costal cartilage is hyaline cartilage with very few cells, and the cells are embedded in the cartilage matrix, which has an immune shielding effect. Chondroitin sulfate and collagen are main ingredients of costal cartilage, and they are safe for using as implant materials. And the amount of other ingredients present is extremely small. Transplantation of costal cartilage is often used for reconstruction of auricle and trachea. The junction between the rib and the cartilage is used to help repair and reconstruction of cartilage injuries in interphalangeal joints, metacarpophalangeal joints, mandibular joints, elbow joints and wrist joints. In addition, Chinese patents No. 201910330808.9 and 201310192619.2 disclose the use of costal cartilage for repair of articular cartilage defects. Costal cartilage has mechanical properties similar to those of articular cartilage, so there is almost no immune rejection reaction, and costal cartilage can form a stable biological bond with the bone bed.

In conclusion, costal cartilage is suitable for use in repair and fixation of articular cartilage, such as fragmented or broken osteochondral bone blocks on articular surfaces, autologous transplantation for repair of osteochondral columns. However, there are no reports on the practice of cutting costal cartilage into cartilage rods or cartilage spicule for fragmented or broken osteochondral bone blocks on articular surfaces, autologous transplantation for repair of osteochondral columns. Moreover, devices that assist to the fixation of cartilage rods need to be improved.

SUMMARY

Given that the foregoing problems exist in the prior art, the present invention provides a device, a kit for repairing and fixing articular cartilage, and a method for the same. The surface of the cartilage rod can be cut into a desired shape which fits to the articular surface, and has biomechanical properties similar to those of articular cartilage; the deep part of the cartilage rod and the cancellous bone of the bone bed form a biological osteochondral interface to achieve a stable long-term biological fixation. By using the method, the biological properties of materials for fixation of cartilage on the articular surface is greatly improved, and osteochondral dislocation can be avoided during its operation.

For the above-mentioned purposes, the present invention adopts the following technical solutions:

According to a first aspect of the invention, there is provided a device for repairing and fixing articular cartilage is provided, comprising: a costal cartilage rod, an outer sleeve, a drilling part, and an auxiliary implantation component;
  wherein the drilling part comprises a drill sleeve and a drill bit matching an inner diameter of the drill sleeve; the auxiliary implantation component comprises a cartilage rod sleeve and an auxiliary pushing element.

Furthermore, the costal cartilage rod has a rod-shaped structure with a diameter ranging from 3 mm to 8 mm and less than an inner diameter of the cartilage rod sleeve, and the costal cartilage rod is obtained from processing of costal cartilage.

Furthermore, the costal cartilage is selected from the group consisting of autologous costal cartilage, allogeneic costal cartilage, or xenogeneic costal cartilage.

Furthermore, a bottom end of the outer sleeve is provided with serrations to prevent sliding.

Furthermore, the drill sleeve and the cartilage rod sleeve have an outer diameter equal to an inner diameter of the outer sleeve.

Furthermore, each of the drill sleeve and the cartilage rod sleeve has a limiting component at its upper end.

Furthermore, the outer sleeve, the drill sleeve, and the cartilage rod sleeve are made of metals.

Furthermore, the auxiliary pushing element is a metal cylinder with a diameter smaller than or equal to a diameter of the costal cartilage rod.

Furthermore, a top end of the metal cylinder is provided with a handle; the handle is in the shape of a circular disk or cuboid.

According to a second aspect of the invention, there is provided a kit for repairing and fixing articular cartilage is provided, comprising the device as described in the first aspect and parts for fixing and clamping the respective components in the device.

Furthermore, the kit has a gradient cartilage rod; the gradient cartilage rod is prepared by mixing chitosan and HA.

According to a third aspect of the invention, there is provided a method for repairing and fixing articular cartilage using the kit as described in the second aspect, comprising the steps of:
  Step 1, applying a force to fix the outer sleeve to articular cartilage to be fixed, inserting the drill bit into the drill sleeve, embedding the drill sleeve into the outer sleeve, and drilling a hole with a desired depth;
  Step 2, upon the completion of the drilling, removing the drill sleeve, inserting the costal cartilage rod sleeved with the cartilage rod sleeve into the outer sleeve, and implanting the costal cartilage rod into the drilled hole by using the auxiliary pushing element; and
  Step 3, removing the device, and cutting the costal cartilage rod to a level which is flush with the articular surface.

Furthermore, the depth that the drill bit penetrates into the articular cartilage is the same as a length of the costal cartilage rod remaining in the articular cartilage to be fixed.

Furthermore, the above-mentioned method further comprises auxiliary fixing, by the gradient cartilage rod, at a non-load bearing area of the articular cartilage to be fixed.

By adopting the above-mentioned technical solutions, the present invention has the following beneficial effects:

Costal cartilage is processed into a costal cartilage rod by using the device provided in the present invention. The costal cartilage rod can form a good biological bonding interface with the articular cartilage to be fixed and a bone bed. In addition, sufficient costal cartilage available for processing into the costal cartilage rod, so it is easy to cut the costal cartilage into desired forms and can be mass-produced. The surface of the cartilage rod can be cut into a desired shape which fits to the articular surface, and has biomechanical properties similar to those of articular cartilage; the deep part of the cartilage rod and the cancellous bone of the bone bed form a biological osteochondral interface to achieve a stable long-term biological fixation. The method according to the present invention is easy to operate and provides a new strategy for repair of femoral cartilage-related injuries.

BRIEF DESCRIPTION OF THE DRAWINGS

The accompanying drawings, together with the specification, illustrate exemplary embodiments of the present disclosure, and, together with the description, serve to explain the principles of the present invention.

In the accompanying drawings: 1—outer sleeve, 11—serration, 2—drill sleeve, 21—first limiting component, 3—drill bit, 4—cartilage rod sleeve, 41—second limiting component, 5—costal cartilage rod, 6—auxiliary pushing element.

DETAILED DESCRIPTION

In the early stage of inventor's study, animal experimentation has proven that costal cartilage can form a stable biological bond with the bone bed after transplantation, and absorbable materials leave a cavity. It is known that costal cartilage has biomechanical and histological properties similar to those of the articular cartilage, it is less likely to cause osteoarthritis; it has immune shielding effects and is not prone to cause immune rejection; and it is easy to cut into desired shapes, it is available in a variety of sources. Therefore, based on the above-mentioned advantages, the present invention provides a device for repairing and fixing articular cartilage, comprising: a costal cartilage rod 5, an outer sleeve 1, a drilling part, and an auxiliary implantation component;

wherein the drilling part comprises a drill sleeve 2 and a drill bit 3 matching an inner diameter of the drill sleeve;

the auxiliary implantation component comprises a cartilage rod sleeve 4 and an auxiliary pushing element 6;

the drill sleeve 2 and the cartilage rod sleeve 4 have an outer diameter equal to an inner diameter of the outer sleeve 1.

In a preferred embodiment of the invention, the costal cartilage rod 5 has a rod-shaped structure with a diameter ranging from 3 mm to 8 mm and less than an inner diameter of the cartilage rod sleeve 4, and the costal cartilage rod is obtained from processing of costal cartilage.

In a preferred embodiment of the invention, the costal cartilage is one selected from the group consisting of autologous costal cartilage, allogeneic costal cartilage, or xenogeneic costal cartilage. In the case of autologous costal cartilage, the costal cartilage refers to 5-7 ribs, preferably the sixth costal cartilage on the right side; while in the case of allogeneic costal cartilage or xenogeneic costal cartilage, the cartilage is any horizontal costal cartilage.

In a preferred embodiment of the invention, a bottom end of the outer sleeve 1 is provided with serrations 11 to prevent sliding.

In a preferred embodiment of the invention, each of the drill sleeve 2 and the cartilage rod sleeve 4 is fixed a limiting component at its upper end for preventing the overextension of the drill sleeve 2 and the cartilage rod sleeve 4 from causing unnecessary load-bearing and injuring on bone joints. And when only one medical staff is present, it may help him/her better apply a force or make an observation.

In a preferred embodiment of the invention, the outer sleeve 1, the drill sleeve 2, and the cartilage rod sleeve 4 are made of metals.

In a preferred embodiment of the invention, the auxiliary pushing element 6 is a metal cylinder with a diameter slightly smaller than or equal to a diameter of the costal cartilage rod 5.

The invention further provides a kit for repairing and fixing articular cartilage, comprising the device as described in the first aspect and parts for fixing and clamping all the components in the device.

In a preferred embodiment of the invention, the kit has a gradient cartilage rod; the gradient cartilage rod is prepared by mixing chitosan and HA.

In addition, the invention further provides a method for repairing and fixing articular cartilage using the device and the kit as described above.

The invention will become more apparent from the following detailed description by way of embodiments, taken in conjunction with the accompanying drawings, however, the following embodiments are not intended to limit the scope of the invention.

Example 1

Figure 1:
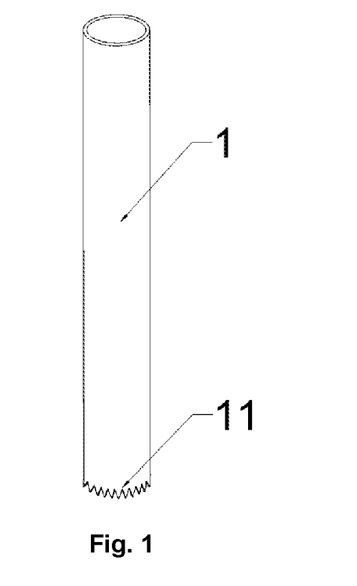
FIG. 1 is a schematic diagram showing an outer sleeve in a device for repairing and fixing articular cartilage according to an embodiment of the present invention.
Figure 2:
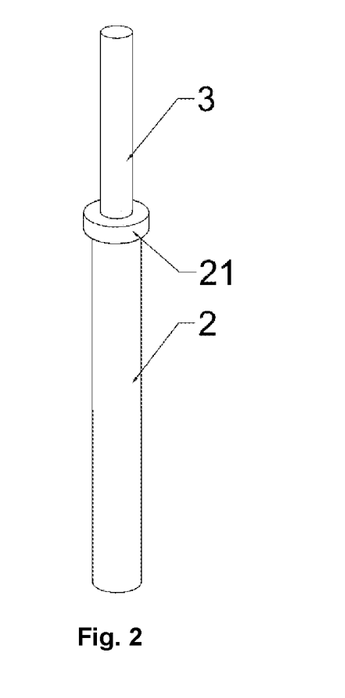
FIG. 2 is a schematic diagram showing an assembly process of drilling part in a device for repairing and fixing articular cartilage according to an embodiment of the present invention.
Figure 3:
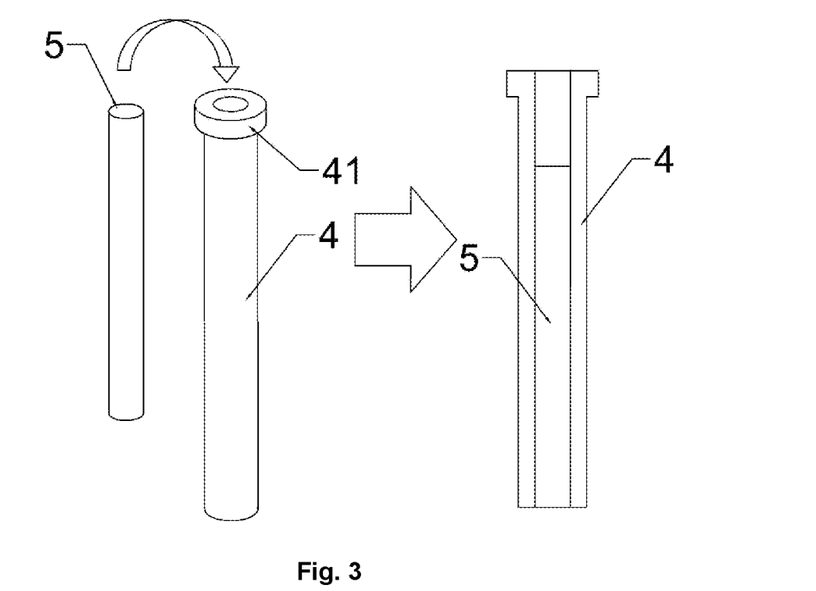
FIG. 3 is a schematic diagram showing an auxiliary implantation component (in a state where a costal cartilage rod is not inserted and inserted) in a device for repairing and fixing articular cartilage according to an embodiment of the present invention.
Figure 4:
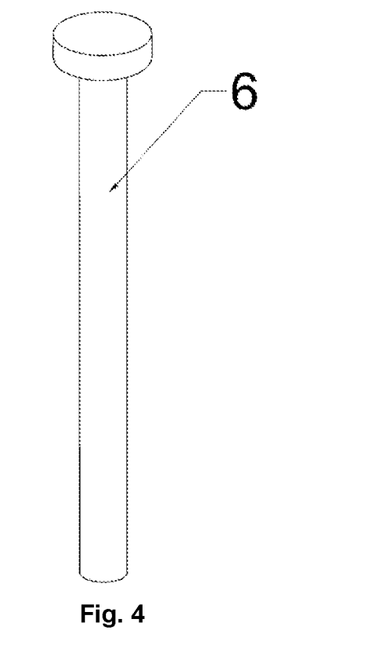
FIG. 4 is a schematic diagram showing an auxiliary pushing element in a device for repairing and fixing articular cartilage according to an embodiment of the present invention.
Figure 5:
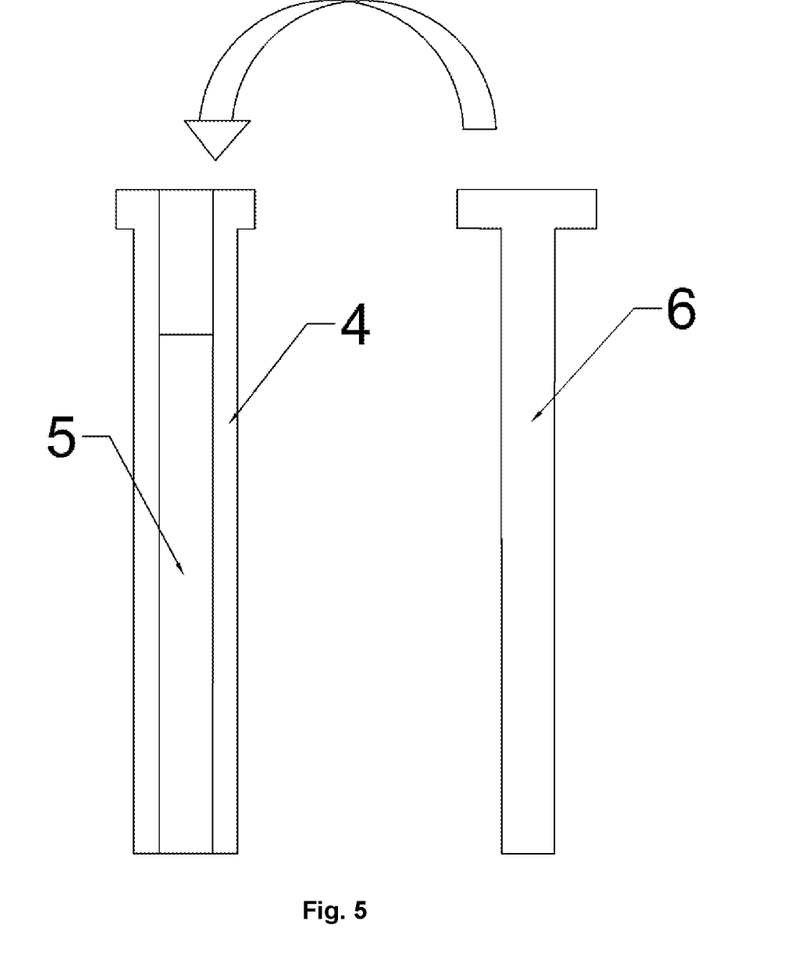
FIG. 5 is a schematic diagram showing an assembly process of implantation of a costal cartilage rod with the auxiliary pushing element according to an embodiment of the present invention.

As shown in FIGS. 1-5, this embodiment provides a device for repairing and fixing articular cartilage, comprising: a costal cartilage rod 5, an outer sleevel, a drilling part, and an auxiliary implantation component;

as shown in FIG. 1, a bottom end of the outer sleeve 1 is provided with serrations 11 evenly arranged to prevent sliding; the outer sleeve 1 is made of metal;

as shown in FIG. 2, the drilling part comprises a drill sleeve 2 having a length slightly smaller than or equal to that of the outer sleeve 1 and a drill bit 3 matching an inner diameter of the drill sleeve; an upper end of the drill sleeve 2 is provided with a limiting component 21, the limiting component 21 is a raised collar structure that can be integrated with the drill sleeve 2 and is made of metal; the length of the drill bit 3 is greater than the length of the drill sleeve 2, and the diameter of the drill bit 3 is equal to the inner diameter of the drill sleeve 2;

as shown in FIGS. 3-5, the auxiliary implantation component comprises a cartilage rod sleeve 4 with a length slightly smaller than or equal to that of the outer sleeve 1, and an auxiliary pushing element 6; an upper end of the cartilage rod sleeve 4 is provided with a second limiting component 41, the limiting component 41 is a raised collar structure that can be integrated with the cartilage rod sleeve 4 and is made of metal; the length of the costal cartilage rod 5 is smaller than or equal to the length of the cartilage rod sleeve 4, and the diameter of the costal cartilage rod 5 is slightly smaller than the inner diameter of the cartilage rod sleeve 4 and is equal to the diameter of the drill bit 3; the costal cartilage rod 5 has a rod-shaped structure with a diameter ranging from 3 mm to 8 mm, and costal cartilage (one selected from the group consisting of autologous costal cartilage, allogeneic costal cartilage, or xenogeneic costal cartilage) is cut and processed into the costal cartilage rod 5, and its diameter and length can be varied upon the desired applications;

in addition, the auxiliary pushing element 6 is a metal cylinder with a diameter slightly smaller than or equal to a diameter of the costal cartilage rod 5; and a top end of the auxiliary pushing element 6 is provided with a handle; the handle is in the shape of a circular disk or cuboid.

Example 2

Figure 6:
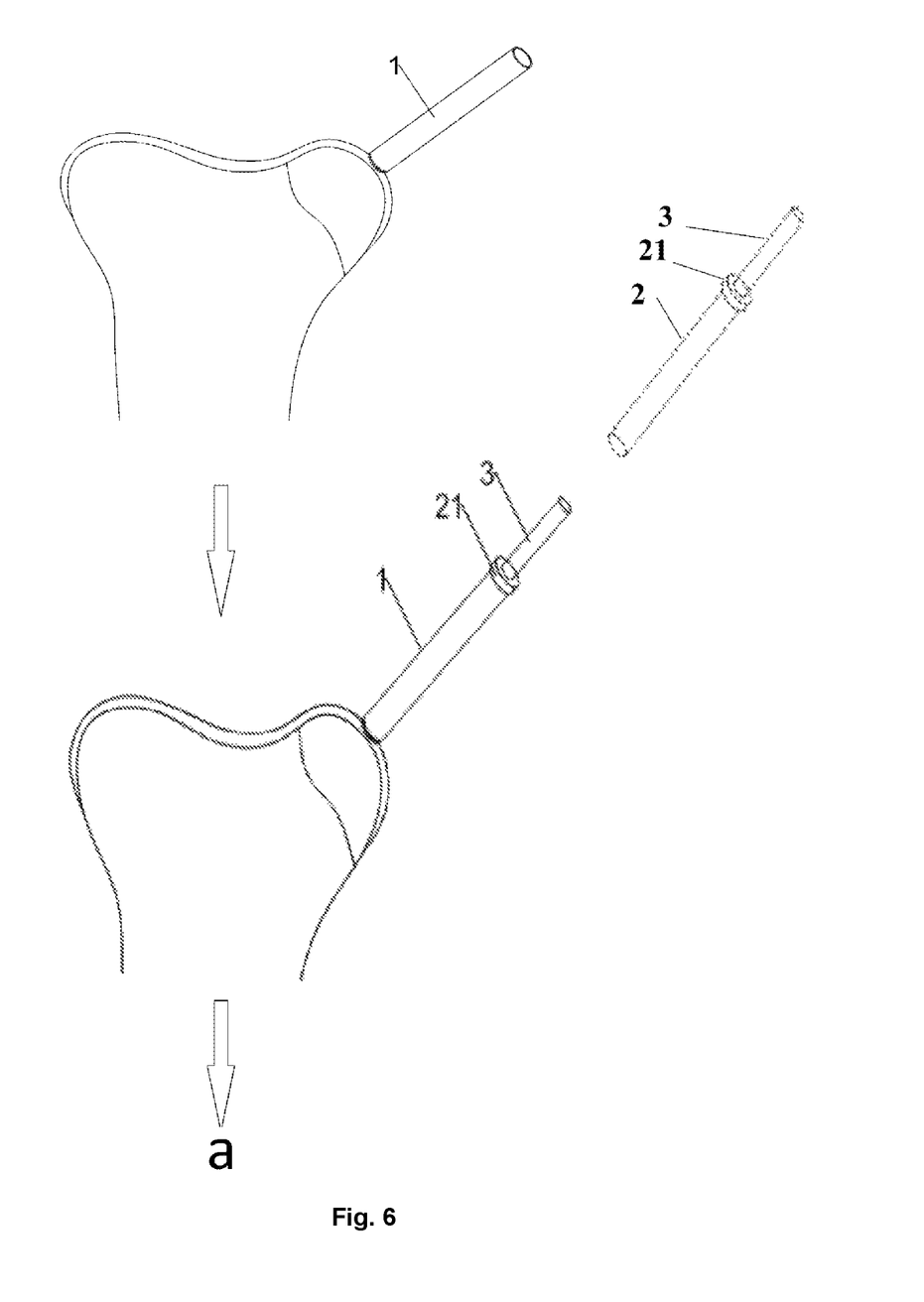
FIG. 6 is a flowchart of a method for repairing and fixing articular cartilage according to an embodiment of the present invention.

Referring to FIG. 6, this embodiment provides a method for fixing exfoliated articular surface osteochondral block using the device as described in the Example 1, comprising the steps of:

Step 1, applying a force to fix the outer sleeve 1 to articular cartilage to be fixed, inserting the drill bit 3 into the drill sleeve 2, embedding the drill sleeve 2 into the outer sleeve 1, and drilling a hole with a desired depth;

Step 2, upon the completion of the drilling, removing the drill sleeve 2, inserting the costal cartilage rod 5 sleeved with the cartilage rod sleeve 4 into the outer sleeve 1, and implanting the costal cartilage rod 5 into the drilled hole by aligning the auxiliary pushing element 6 to the implanting costal cartilage rod 5; and Step 3, removing the device, and cutting a portion of the costal cartilage rod 5 which is over the articular surface so that the costal cartilage rod 5 is flush with the articular surface.

Example 3

This embodiment provides a kit for repairing and fixing articular cartilage is provided, comprising the device as described in the Example 1 (as shown in FIGS. 1-5), and parts for fixing and clamping the respective components in the device and a plurality of gradient cartilage rods, wherein the gradient cartilage rod is prepared by mixing chitosan and HA.

Example 4

This embodiment adopts a method for fixing broken articular surface osteochondral block by using the kit provided in Example 3, comprising the steps of:

Step 1, applying a force to fix the outer sleeve 1 to a load-bearing part of articular cartilage to be fixed, inserting the drill bit 3 into the drill sleeve 2, embedding the drill sleeve 2 into the outer sleeve 1, and drilling a hole on the articular cartilage with a desired depth;

Step 2, upon the completion of the drilling, removing the drill sleeve 2, inserting the costal cartilage rod 5 sleeved with the cartilage rod sleeve 4 into the outer sleeve 1, and implanting the costal cartilage rod 5 into the drilled hole by aligning the auxiliary pushing element 6 to the costal cartilage rod 5;

Step 3, removing the device, and cutting a portion of the costal cartilage rod 5 which is over the articular surface so that the costal cartilage rod 5 is flush with the articular surface; and Step 4, adopting the method comprising the Steps 1-3, the costal cartilage rod 5 is replaced with a gradient cartilage rod, so the articular cartilage is reinforced at its non-load bearing part.

The above descriptions are only the preferred embodiments of the invention, not thus limiting the embodiments and scope of the invention. Those skilled in the art should be able to realize that the schemes obtained from the content of specification and drawings of the invention are within the scope of the invention.

What is claimed is:

1. A kit for repairing and fixing articular cartilage, comprising: a costal cartilage rod, an outer sleeve, a drilling part, an auxiliary implantation component, and a gradient cartilage rod;

wherein the costal cartilage rod is configured to be fixed at a load-bearing area of the articular cartilage;

wherein the drilling part comprises a drill sleeve and a drill bit matching an inner diameter of the drill sleeve;

wherein the auxiliary implantation component comprises a cartilage rod sleeve and an auxiliary pushing element;

wherein the auxiliary pushing element is a metal cylinder with a diameter smaller than or equal to a diameter of the costal cartilage rod, and the auxiliary pushing element has a handle at its top end; and wherein the gradient cartilage rod is configured to be prepared by mixing chitosan and HA, and the gradient cartilage rod is configured to be auxiliary fixed at a non-load bearing area of the articular cartilage.

2. The kit of claim 1, wherein the costal cartilage rod has a rod-shaped structure with a diameter ranging from 3 mm to 8 mm and less than an inner diameter of the cartilage rod sleeve, and the costal cartilage rod is configured to be obtained from processing of costal cartilage.

3. The kit of claim 2, wherein the costal cartilage is selected from the group consisting of autologous costal cartilage, allogeneic costal cartilage, or xenogeneic costal cartilage.

4. The kit of claim 1, wherein a bottom end of the outer sleeve is provided with serrations to prevent sliding.

5. The kit of claim 1, wherein the drill sleeve and the cartilage rod sleeve have an outer diameter equal to an inner diameter of the outer sleeve.

6. The kit of claim 1, wherein the drill sleeve has a first limiting component at its upper end, and the cartilage rod sleeve has a second limiting component at its upper end; and
wherein the first limiting component is a raised collar structure, and the second limiting component is a raised collar structure.

7. The kit of claim 1, wherein the outer sleeve, the drill sleeve, and the cartilage rod sleeve are made of metals.

8. A method for repairing and fixing articular cartilage using the kit of claim 1, comprising the steps of:
applying a force to fix the outer sleeve to articular cartilage to be fixed, inserting the drill bit into the drill sleeve, embedding the drill sleeve into the outer sleeve, and drilling a hole to a desired depth;
upon the completion of the drilling, removing the drill sleeve, inserting the costal cartilage rod sleeved with the cartilage rod sleeve into the outer sleeve, and implanting the costal cartilage rod into the drilled hole by using the auxiliary pushing element; and
removing the kit, and cutting the costal cartilage rod to a level which is flush with the articular surface.

9. The method of claim 8, wherein the desired depth of the drilled hole is equal to a length of the costal cartilage rod remaining in the articular cartilage to be fixed.

10. The method of claim 8, wherein the costal cartilage rod has a rod-shaped structure with a diameter ranging from 3 mm to 8 mm and less than an inner diameter of the cartilage rod sleeve, and the costal cartilage rod is configured to be obtained from processing of costal cartilage; or
the costal cartilage rod has a rod-shaped structure with a diameter ranging from 3 mm to 8 mm and less than an inner diameter of the cartilage rod sleeve, and the costal cartilage rod is configured to be obtained from processing of costal cartilage, the costal cartilage is selected from the group consisting of autologous costal cartilage, allogeneic costal cartilage, or xenogeneic costal cartilage; or
a bottom end of the outer sleeve is provided with serrations to prevent sliding; or
the drill sleeve and the cartilage rod sleeve have an outer diameter equal to an inner diameter of the outer sleeve; or
each of the drill sleeve and the cartilage rod sleeve has a limiting component at its upper end; or
the outer sleeve, the drill sleeve, and the cartilage rod sleeve are made of metals; or
the auxiliary pushing element is a metal cylinder with a diameter smaller than or equal to a diameter of the costal cartilage rod.

* * * * *